United States Patent
Freedman

(10) Patent No.: US 7,196,517 B2
(45) Date of Patent: Mar. 27, 2007

(54) COMBINING NMR AND DENSITY MEASUREMENTS FOR DETERMINING PROPERTIES OF RESERVOIR FLUID

(75) Inventor: Robert Freedman, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/393,986

(22) Filed: Mar. 30, 2006

(65) Prior Publication Data
US 2006/0181274 A1 Aug. 17, 2006

Related U.S. Application Data

(62) Division of application No. 10/064,727, filed on Aug. 9, 2002, now Pat. No. 7,075,297.

(51) Int. Cl.
*G01V 3/00* (2006.01)
*G01R 33/20* (2006.01)

(52) U.S. Cl. .................. 324/306; 324/303
(58) Field of Classification Search .............. None
See application file for complete search history.

(56) References Cited

U.S. PATENT DOCUMENTS

| 4,782,295 A * | 11/1988 | Lew | 324/306 |
|---|---|---|---|
| 4,785,245 A * | 11/1988 | Lew et al. | 324/308 |
| 4,901,018 A * | 2/1990 | Lew | 324/306 |
| 5,122,746 A * | 6/1992 | King et al. | 324/307 |
| 6,032,101 A * | 2/2000 | Freedman et al. | 702/8 |
| 6,046,587 A * | 4/2000 | King et al. | 324/306 |
| 6,147,489 A * | 11/2000 | Freedman et al. | 324/303 |
| 6,255,819 B1 * | 7/2001 | Day et al. | 324/303 |
| 6,268,727 B1 * | 7/2001 | King et al. | 324/306 |
| 6,337,568 B1 * | 1/2002 | Tutunji et al. | 324/303 |
| 6,646,437 B1 * | 11/2003 | Chitale et al. | 324/303 |
| 6,895,107 B2 * | 5/2005 | Park et al. | 382/133 |
| 7,032,661 B2 * | 4/2006 | Georgi et al. | 166/250.01 |
| 7,075,297 B2 * | 7/2006 | Freedman | 324/303 |
| 2004/0032257 A1 * | 2/2004 | Freedman | 324/303 |
| 2004/0055745 A1 * | 3/2004 | Georgi et al. | 166/250.02 |
| 2006/0181274 A1 * | 8/2006 | Freedman | 324/306 |

FOREIGN PATENT DOCUMENTS

WO  WO/9859220  * 12/1998

* cited by examiner

*Primary Examiner*—Brij Shrivastav
*Assistant Examiner*—Tiffany A. Fetzner
(74) *Attorney, Agent, or Firm*—Bryan L. White; Kevin P. Mcenaney; William Batzer

(57) ABSTRACT

A method for evaluating formation fluids includes measuring a nuclear magnetic resonance property related to a total volume of the formation fluids, measuring a dielectric property related to an electromagnetic wave travel time, measuring a bulk density, and solving a set of linear response equations representing a reservoir fluid model to determine fractional fluid volumes from the nuclear magnetic resonance property, the dielectric property, and the bulk density.

2 Claims, 3 Drawing Sheets

COMBINING NMR AND DENSITY MEASUREMENTS FOR DETERMINING PROPERTIES OF RESERVOIR FLUID

This application is a divisional of U.S. patent application Ser. No. 10/064,727 filed Aug. 9, 2002, published on Feb. 19, 2004 as U.S. patent application publication number 2004/0032257A1, and issued as U.S. Pat. No. 7,075,297 on Jul. 11, 2006.

BACKGROUND OF INVENTION

1. Field of the Invention

The disclosed subject matter relates generally to well log interpretation. More specifically, this invention relates to using combinations of well logging measurements to derive reservoir fluid volumes and rock properties.

2. Background Art

One type of tool used for investigating a formation around a borehole is a nuclear magnetic resonance ("NMR") logging tool. NMR tools are well known in the art. They measure the relaxation rates of hydrogen atoms in the pore spaces of earth formations by detecting the amplitude and decay rate of signals resulting from pulsed NMR spin-echo sequences. The NMR tool emits a sequence of radio-frequency pulses into the formation and then monitors the returning pulses, which are called "spin-echoes." The amplitude of the spin-echoes measured by the NMR tool are proportional to the mean density of hydrogen nuclei in the fluid that occupies the pore spaces in the NMR tool's volume of investigation. Because the hydrogen densities in water and in liquid hydrocarbons are approximately the same, the detected NMR signal is proportional to the volume fraction of liquid occupying the pore space. One such NMR tool is described in U.S. Pat. No. 6,147,489 to Freedman et al.

In gas-bearing formations, NMR derived formation porosity is too low because of the low hydrogen index of gas compared to that of water. Similarly in reservoirs containing very viscous or heavy oil the NMR derived porosity is too low. The porosity deficit is caused by the very short relaxation times in heavy oils. That is, the signals decay so fast that significant signal amplitude is lost before the first spin-echo is detected. In formations that do not contain gas or very viscous oil, the NMR signal is related to the total porosity of the formation. The porosity determined by the NMR measurement is governed by:

$$\phi_{nmr} = \phi_0(H_o P_o - H_w P_w) + \phi H_w P_w \quad (1)$$

where $\phi_{nmr}$ is the measured NMR porosity, $\phi_0$ is the oil filled porosity, $\phi$ is the total rock porosity, $P_w$ and $P_o$ are polarization functions for water and oil, and $H_w$ and $H_o$ are the hydrogen indices of water and oil.

As is known in the art, the polarization function accounts for the degree of magnetization that is achieved during the wait time (W) that precedes each measurement. The measurable magnetization depends on the longitudinal relaxation time (T1) of the fluid and W. By selecting a sufficiently long wait time between experiments, the polarization functions can be made to approach 1 (i.e., $P_w \cong P_o \cong 1$). Because it is often true in practice that the hydrogen indices of water and oil are about one (i.e. $H_w \cong H_o \cong 1$), Equation 1 reduces to:

$$\phi_{nmr} \cong \phi \quad (2)$$

Thus, the total NMR porosity measured by an NMR tool in an oil-bearing formation is typically close to the formation porosity.

Another tool used for investigating a formation traversed by a borehole is a microwave or high-frequency dielectric tool. Often called electromagnetic propagation tools, dielectric tools are well known in the art. Microwave or high-frequency dielectric measurements have been used since the late 1970s to provide estimates of the fluid saturations in the flushed zone adjacent to a borehole drilled into an earth formation. A typical electromagnetic propagation tool has transmitters and receivers located on a pad placed in contact with the borehole wall. The transmitters transmit microwaves or high-frequency electromagnetic radiation into the formation penetrated by the borehole. The receivers, located in at least one additional location on the pad, measure the phase shift and attenuations of the radiation as it propagates through the formation. The phase shift and attenuation measurements can be inverted using models to obtain formation travel times $t_{pl}$ and attenuations $A_t$ of the electromagnetic fields propagating in the formation (Freedman and Vogiatzis, Geophysics 44, no. 10, 969–986, 1979). The travel times for some minerals and fluids commonly found in earth formations are shown in Table 1. (Schlumberger Log Interpretation Principles, 1987, p. 126).

| Mineral or Fluid | Travel Time (ns/m) |
| --- | --- |
| Sandstone | 7.2 |
| Dolomite | 8.7 |
| Limestone | 9.1–10.2 |
| Anhydrite | 8.4 |
| Halite | 7.9–8.4 |
| Gypsum | 6.8 |
| Shale | 7.45–16.6 |
| Oil | 4.7–5.2 |
| Gas | 3.3 |
| Water | 25–30 |

Because the dielectric constant of water is much higher than the dielectric constants of hydrocarbons and the formation matrix material, the measured travel time is mostly dependent on the fraction of water in the formation.

The measured formation travel times can be related via a theoretical equation:

$$\tilde{t}_{pl} = \tilde{t}_{pw} \phi - \phi_0(t_{pw} - t_{po}) \quad (3)$$

where $\tilde{t}_{pl} = t_{pl} - t_{pma}$, $\tilde{t}_{pw} = t_{pw} - t_{pma}$, $t_{pl}$ is the travel time measured by the tool, $t_{pw}$ is the brine travel time. The brine travel time is a function of temperature (T) and salinity (s), $t_{pma}$ is the travel time of the rock matrix, $t_{po}$ is the travel time of the crude oil, $\phi$ is the total formation porosity, and $\phi_0$ is the oil-filled porosity. The travel times are the inverse phase velocities of electromagnetic wave propagation in the respective media. Equation 3 represents a "dielectric mixing law" that relates the constituent travel times to the formation travel times. Other mixing laws can be derived that serve the same purpose.

Density logs are another type of wellbore measurement that are well known in the art. A density logging tool contains a radioactive source that emits medium-energy gamma ray radiation into the formation. The density logging tool also contains a detector at some distance away from the source. Due to Compton scattering with atomic electrons in the formation, the gamma rays lose energy as they propagate through the formation. The decrease in the gamma ray energy is related to the electron density in the formation, and, thus, is also generally related to the formation bulk density $\rho_b$. The bulk density can be related to the porosity of the formation by the following equation:

$$\rho_b = \phi\rho_f + (1-\phi)\rho_{ma} \quad (4)$$

where $\rho_f$ is the average density of the fluid in the pore spaces, $\rho_{ma}$ is the density of the rock matrix, and $\phi$ is the formation porosity.

The NMR, density, and dielectric measurements and equations discussed above are applicable to measurements made in earth formations by conventional logging tools. The conventional tools include wireline logging tools and logging while drilling ("LWD") tools. For dielectric measurements of reservoir fluids in rocks, it is important to make high-frequency measurements in order to avoid complicated dispersion or frequency dependent effects that cloud the interpretation of low-frequency dielectric measurements in reservoir rocks.

The NMR, density, and dielectric measurements can also be performed on samples of bulk fluids withdrawn from the formation by a fluid sampling tool like the Schlumberger Modular Dynamics Tester (MDT) tool or similar tool. These tools are discussed in several recent patents (Kleinberg, U.S. Pat. No. 6,346,813 B; Prammer, U.S. Pat. No. 6,107,796; Edwards, et al., U.S. Pat. No. 6,111,409; Blades and Prammer, U.S. Pat. No. 6,111,408). A fluid sampling tool typically uses packers to isolate a portion of the borehole wall. The pressure within the packers is reduced until the formation fluid flows into the sampling tool. Another type of sampling tool uses a probe that is inserted into or pressed against the formation, and fluid is withdrawn. Usually, the formation fluid is monitored, with an optical device for example, until there is no change in the formation fluid flowing into the sampling tool. At that point, it is assumed that the formation fluid that is flowing into the sampling tool does not contain any mud or mud filtrate and is comprised substantially of native formation fluids.

The equations discussed above and in the following sections of this patent are valid for NMR, density, and dielectric measurements made on bulk fluids in a sample module or flow line of a tool like the MDT that can be equipped with NMR, density, and dielectric measuring sensors. The sensors can be placed in the flow line so that the measurements are made while the fluids are in motion. Alternatively, a fluid sample can be diverted to a measurement cell where the measurement can be made on the stationary fluid. For measurement of bulk fluid dielectric properties it is not necessary to operate at high frequencies because there is negligible dispersion in the dielectric properties at lower frequencies. The equations for bulk fluids measured outside the formation can be obtained from equations appropriate for rocks by simply setting the rock matrix parameters to zero. That is, for bulk fluids, $\rho_{ma}=0$ and $t_{pma}=0$ in the above equations.

SUMMARY OF INVENTION

One aspect of an embodiment of the disclosed subject matter relates to methods for evaluating formation fluids. A method of an embodiment of the disclosed subject matter includes acquiring a nuclear magnetic resonance measurement of the formation fluids, acquiring a dielectric measurement of the formation fluids, and determining an oil volume fraction of the formation fluids.

Another aspect of an embodiment of the disclosed subject matter relates to methods for evaluating the volume of formation fluids. A method of an embodiment of the disclosed subject matter includes acquiring a nuclear magnetic resonance measurement, acquiring a dielectric measurement related to an electromagnetic travel time, acquiring a bulk density measurement, and solving a set of linear response equations representing a reservoir fluid model to determine fractional fluid volumes from the nuclear magnetic resonance property, the dielectric property, and the bulk density.

Another aspect of an embodiment of the disclosed subject matter relates to methods for evaluating formation fluids from a gas-bearing formation. A method of an embodiment of the disclosed subject matter includes acquiring a bulk density measurement, acquiring a dielectric measurement, and determining a gas-corrected fluid volume.

Another aspect of an embodiment of the disclosed subject matter relates to methods for evaluating a formation traversed by a borehole. A method of an embodiment of the disclosed subject matter includes acquiring a nuclear magnetic resonance measurement, acquiring a dielectric property measurement related to a formation traveltime, and determining a rock-matrix travel time from the nuclear magnetic resonance measurement and the dielectric measurement.

Another aspect of an embodiment of the disclosed subject matter related to methods for evaluating a formation traversed by a borehole. A method of an embodiment of the disclosed subject matter includes acquiring a dielectric measurement and determining a dielectric-derived water volume, acquiring a suite of NMR measurements and determining a water volume and an apparent heavy oil volume, and comparing the dielectric-derived water volume with the NMR derived water volume and the apparent heavy oil volume to produce a true heave oil volume.

Other aspects and advantages of an embodiment of the disclosed subject matter will be apparent from the following description and the appended claims.

DETAILED DESCRIPTION

Figure 2:
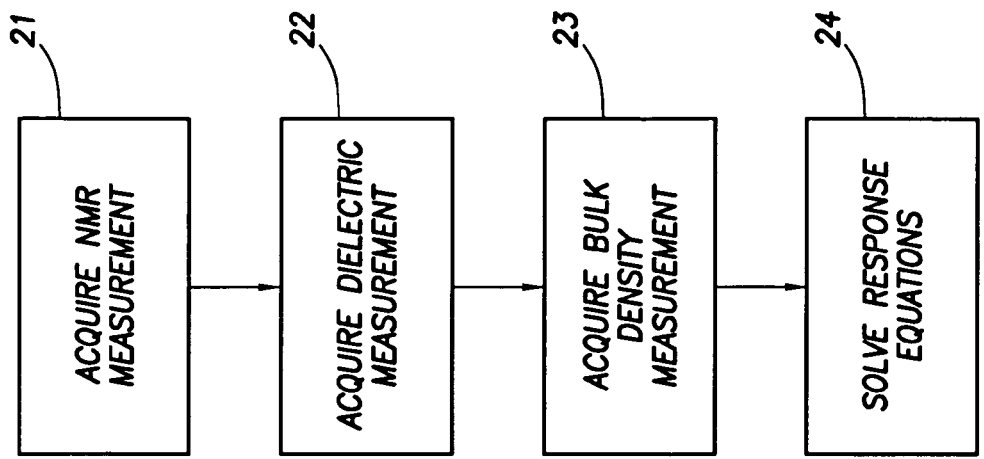
FIG. 2 is a flow chart showing another embodiment of a method according to an embodiment of the disclosed subject matter.

In an oil-bearing reservoir the oil-filled porosity can be determined more accurately by using the NMR and dielectric tools described in the Background section herein. By solving Equations 1 and 3 for the oil-filled porosity $\phi_o$, the following is obtained:

$$\phi_o = \frac{\phi_{nmr}(t_{pw} - t_{pma}) - (t_{p1} - t_{pma}) H_w P_w}{(t_{pw} - t_{pma}) H_o P_o + (t_{pma} - t_{po}) H_w P_w} \quad (5)$$

where $t_{pl}$ is the travel time measured by the tool, $t_{pw}$ is the brine travel time and is a known function of temperature (T) and brine salinity (s), $t_{pma}$ is the travel time of the rock matrix, $t_{po}$ is the travel time of the crude oil, $H_w$ and $H_o$ are the hydrogen indices of water and oil, $P_w$ and $P_o$ are polarization functions for water and oil, and $\phi_o$ is the oil-filled porosity.

It is understood by those skilled in the art that Equations 3 and 5 imply a particular choice of "dielectric mixing law." A dielectric mixing law is a mathematical model that relates the travel times of the constituents of the formation (i.e. the brine travel time $t_{pw}$, the rock matrix travel time $t_{pma}$, and the crude oil travel time $t_{po}$) to the total formation travel time $t_{pl}$. Those skilled in the art will realize that other mixing laws can be employed within the scope of this invention. It is also recognized by those skilled in the art that the travel times relate to composites of the real and the imaginary parts of a complex dielectric constant. Although the dielectric measurements are expressed here in terms of travel times and attenuations, these quantities can equivalently be cast in terms of the real and imaginary parts of a complex dielectric constant without departing from the scope of the disclosed subject matter.

By choosing NMR polarization times sufficiently long so that all fluids are substantially polarized, the polarization functions are equal to about one (i.e. $P_w \cong P_0 \cong 1$). Because it is often true in practice that the hydrogen indices of water and oil are about one (i.e. $H_w \cong H_o \cong 1$), Equation 5 can be reduced to:

$$\phi_o = \phi_{nmr}\left(\frac{t_{pw} - t_{pma}}{t_{pw} - t_{po}}\right) - \left(\frac{t_{p1} - t_{pma}}{t_{pw} - t_{po}}\right) \quad (6)$$

Because the dielectric constant of water is much greater than the dielectric constants for hydrocarbons and the rock matrix material, the travel times in oil and the rock matrix are approximately equal when compared to the travel time in water (i.e., $t_{po} \cong t_{pma}$) Thus, Equation 6 approximately reduces to:

$$\phi_o \approx \phi_{nmr} - \phi_{diel} \quad (7)$$

where $\phi_{diel}$ is the porosity computed from the dielectric travel time measurement in a water zone and is given by:

$$\phi_{diel} = \frac{t_{p1} t_{pma}}{t_{pw} - t_{pma}}. \quad (8)$$

Equation 7 shows that in oil-bearing formations the oil-filled porosity $\phi_o$ is approximately equal to the difference between the NMR total porosity $\phi_{nmr}$ and the porosity computed from the dielectric measurement $\phi_{diel}$.

The total formation porosity $\phi$ can be obtained by solving Equations 1 and 3:

$$\phi = \frac{\phi_{nmr}(t_{pw} - t_{po}) + (t_{p1} - t_{pma})(H_o - H_w)}{(t_{pw} - t_{pma}) H_o + (t_{pma} - t_{po}) H_w} \quad (9)$$

As noted above, when the hydrogen indices of water and oil are assumed to be equal to about one (i.e. $H_w \cong H_o \cong 1$), as is often the case in practice, Equation 9 reduces to $\phi \cong \phi_{nmr}$, as shown in Equation 2. The water-filled porosity is equal to the difference between the total porosity and the oil-filled porosity (i.e., $\phi_w = \phi - \phi_o$). Thus, subtracting Equation 6 from Equation 9 the water-filled porosity is given by:

$$\phi_w = \frac{\phi_{nmr}(t_{pw} - t_{po}) + (t_{p1} - t_{pma})(H_o - H_w)}{(t_{pw} - t_{pma}) H_o + (t_{pma} - t_{po}) H_w} \quad (10)$$

Again, reducing Equation 10 for the condition where $H_w \cong H_o \cong 1$ provides:

$$\phi_w = \phi_{nmr}\left(\frac{t_{pma} - t_{po}}{t_{pw} - t_{po}}\right) + \left(\frac{t_{p1} - t_{pma}}{t_{pw} - t_{po}}\right) \quad (11)$$

Equation 11 shows that the water-filled porosity is primarily determined by the dielectric travel time measurements, with a relatively small amount of weight from the NMR measurement.

The combination of dielectric measurements and NMR measurements can also be used to determine the connate water salinity. The measured formation attenuations $A_c$ are due to losses in the formation and can be related to the water-filled porosity, for example, using the so-called CRIM model (Freedman and Grove, SPE Formation Evaluation Journal, 449–457, December 1990.):

$$A_c = A_w(T, s)\phi_w \quad (12)$$

where $\phi_w$ is the water-filled porosity and, $A_w(T,s)$, is the attenuation of the signal in the brine, which is a known function of temperature (T) and salinity (s) (Dahlberg and Ference, 1971, Transactions of the Society of Professional Well Log Analysts).

In wells drilled with oil-based muds, Equation 12 can be solved for the connate water salinity using an estimate or measurement of the formation temperature. Similarly, in wells drilled with a water-based muds, Equation 12 can be solved for the salinity of the brine in the flushed zone. The water-filled porosity in Equation 12 can be obtained from stand-alone NMR diffusion-based measurements, as described in U.S. Pat. No. 6,229,308 to Freedman. (See also Heaton et al., SPE Paper No. 77400, San Antonio, Tex., September 2002). In a well drilled with an oil-based mud, there are three unknown fluid volumes that it is desirable to determine: (1) the water-filled porosity $\phi_w$, (2) the oil-filled porosity $\phi_o$, and (3) the oil-based mud filtrate filled porosity $\phi_{obmf}$. The solution of this three-fluid model requires at least three formation measurements that measure approximately the same volume in the formation.

Three measurements that are used in one embodiment of the disclosed subject matter are total NMR porosity, bulk density, and travel time. Using these measurements, the three unknown fluid volumes can be calculated with the following system of linear equations:

$$\phi_{nmr} = \sum_{i=1}^{3} \phi_i H_i \qquad (13)$$

$$t_{p1} = \sum_{i=1}^{3} \phi_i t_{pi} + (1-\phi) t_{pma} \qquad (14)$$

$$\rho_b = \sum_{i=1}^{3} \phi_i \rho_i + (1-\phi) \rho_{ma} \qquad (15)$$

where $\rho_o$ is the formation bulk density, $\rho_i$ is the density of the $i^{th}$ fluid, $\rho_{ma}$ is the density of the rock matrix material, $\phi_i$ is the fluid filled porosity of the $i^{th}$ fluid, and $t_{pi}$ is the dielectric travel time travel time of the $i^{th}$ fluid.

Once the three fluid volumes are known, they can be summed to give the total formation porosity:

$$\phi = \sum_{i=1}^{3} \phi_i \qquad (16)$$

where the summations (i=1 to 3) are over the three unknown fluids.

Equations 13–15 assume that the native oil and the oil-based mud filtrate are separate phases and have sufficient contrast in densities, hydrogen indices, and travel times. This assumption, in some circumstances, can be invalid because oil and oil-based mud filtrate are miscible fluids that can mix together into a single fluid. In that case, the above equations can be solved for the brine and oil-filled porosities where the oil-filled porosity includes both native oil and oil-based mud filtrate. Those having skill in the art will realize that the properties of the oil in an oil-based mud can be changed to suit the particular circumstances. An oil-based mud could be devised so that the properties of the mud are different from the properties of the oil to a degree that allows their porosities to be separately detected using these methods. Further, Equation 12 can also be included with Equations 13–16 and the set can be solved simultaneously for the brine salinity and fluid-filled porosities.

In gas-bearing formations drilled with water-based muds, Equations 13–15 can be solved for the gas-filled porosity $\phi_g$, the water filled porosity $\phi_w$, and the gas-corrected total porosity $\phi$. For example, in a gas-bearing formation, the density log and the dielectric log have opposite responses to the presence of gas. Thus, the combination of the density and dielectric logs provides for improved formation evaluation.

In a gas-bearing formation, the density log porosity $\phi_d$ has the form:

$$\phi_d = \phi + \phi_g \left( \frac{\rho_g - \rho_w}{\rho_w - \rho_{ma}} \right) \qquad (17)$$

Equation 17 shows that, in a gas-bearing formation, the density log porosity over-estimates the actual formation porosity because in practice the second term on the right hand side of Equation 17 is positive.

The dielectric travel time response in Equation 14 can be written for a gas-bearing formation as follows:

$$t_{p1} = t_{pw} \phi - \phi_g (t_{pw} - t_{pg}) \qquad (18)$$

Equation 18 shows that the dielectric travel time is decreased in a gas-bearing formation.

The opposite responses to the presence of gas in the formation from the density measurement and the dielectric measurement can be used to compute a gas-corrected total formation porosity. Solving Equations 17 and 18 for the gas-filled porosity yields:

$$\phi_g = \frac{\phi_d - \phi_{diel}}{\frac{\rho_g - \rho_w}{\rho_w - \rho_{ma}} + \frac{t_{pw} - t_{pg}}{t_{pw} - t_{pma}}} \qquad (19)$$

where $\phi_{diel}$ is the dielectric derived total porosity in a water-bearing zone as defined in Equation 8. Equation 20 shows the relationship again:

$$\phi_{diel} = \frac{t_{p1} - t_{pma}}{t_{pw} - t_{pma}} \qquad (20)$$

Solving for the gas-corrected total formation porosity yields:

$$\phi = w\phi_d + (1-w)\phi_{diel} \qquad (21)$$

where w is a weighting function given by:

$$w = \left[ 1 + \left( \frac{\rho_g - \rho_w}{\rho_w - \rho_{ma}} \right) \left( \frac{t_{pw} - t_{pma}}{t_{pw} - t_{pg}} \right) \right]^{-1} \qquad (22)$$

Again, the weighting function is derived from the dielectric mixing law. Because the dielectric mixing law is a matter of choice, those skilled in the art will realize the particular mixing laws and weighting functions are not meant to limit the scope of the disclosed subject matter.

Equations 19 and 21 have a similar form to equations derived by combining density and NMR logs in gas-bearing reservoirs (Freedman et al., U.S. Pat. No. 6,147,489).

The above equations and methods are easily adapted to the analysis of measurements made on bulk fluids in a downhole fluid sampling tool. For bulk fluids, the fluid-filled porosities $\phi_i$ in Equations 13–15 become fractional volumes whose summation is equal to one. It is also understood by those skilled in the art that the dielectric measurement made in the fluid sampling tool does not have to be an electromagnetic propagation measurement. The dielectric properties of the fluid sample can be measured using other well-known laboratory methods, e.g., by putting the sample in a waveguide and measuring the S-parameters (e.g., see Ki-Bok Kim et al., IEEE Transactions on Instrumentations and Measurements, vol. 51, no. 1, p. 72–77, February 2002) from which the dielectric constant can be computed, or by measuring the capacitance of the sample, which can be related to the dielectric constant. Similarly, the fluid analysis using bulk density of the sample does not require measuring the Compton scattering of gamma rays. It is understood that fluid bulk densities measured by other means can also be used in the following equations.

For a bulk sample of brine and oil, the oil-filled fractional volume is given by Equation 6, where $t_{pma}$ is set to zero:

$$\phi_o = \phi_{nmr}\left(\frac{t_{pw}}{t_{pw}-t_{po}}\right) - \frac{t_{pl}}{t_{pw}-t_{po}} \cong \phi_{nmr} - \frac{t_{pl}}{t_{pw}} \quad (23)$$

Equation 23 is valid for $H_w \cong H_o \cong 1$. If the hydrogen indices of the brine and oil are not equal, then a more general version of Equation 23 can be obtained by setting $t_{pma}=0$ in Equation 5.

The sum of all the fluid fractions in the sample must equal 1, because the fluid has been removed from the formation. Thus, the water-filled fractional volume is given by, $\phi_w = 1 - \phi_o$. For a bulk sample of brine and gas, the gas-filled fractional volume can be obtained by setting $\rho_{ma}=0$ and $t_{pma}=0$ in Equation 19:

$$\phi_g = \frac{\phi_d - \phi_{diel}}{\left[\frac{t_{pw}-t_{pg}}{t_{pw}} + \frac{\rho_g - \rho_w}{\rho_w}\right]} \quad (24)$$

The dielectric porosity $\phi_{diel}$ in Equation 24 is for bulk fluids and is defined by setting $t_{pma}=0$ in Equation 20:

$$\phi_{diel} = \frac{t_{pl}}{t_{pw}} \quad (25)$$

As noted before, the above equations represent a specific dielectric mixing law and other such laws and equations can also be used within the scope of this invention. In that case the equations in this application are modified accordingly. Other aspects of this invention can also be applied to the measurement of bulk fluid properties in a fluid sampling tool. For example, the dielectric attenuation measurement can be used to estimate the salinity of the brine fraction in the bulk fluid sample withdrawn from the formation.

For bulk fluids the fractional volume of gas in a gas/liquid sample can be computed from Equations 17 and 18 and setting $\rho_{ma}=0$:

$$\phi_g = \frac{\phi_d - \frac{\phi_{nmr}}{H_f}}{\frac{\rho_g}{\rho_f} - \frac{P_g H_g}{H_f}} \quad (26)$$

In the above equation $\rho_g$ and $\rho_f$ are the densities of the gas and liquid components, $H_g$ and $H_f$ are their hydrogen indices and $P_g$ is the gas polarization function. The density porosity, $\phi_d$, in Equation 26 is defined by $$\phi_d = \frac{\rho_b}{\rho_f} \quad (27)$$

In deriving Equation 26 it is assumed that the liquid phase is fully polarized. If this is not the case then Equation 26 can be modified accordingly.

Equation 26 computes the fractional volume of gas from a linear combination of NMR and density porosities. The gas volume fraction can also be computed directly from either the density or NMR measurement. For example, from the density measurement $$\phi_g = \frac{\phi_d - 1}{\frac{\rho_g}{\rho_f} - 1} \quad (28)$$

and from the NMR measurement:

$$\phi_g = \frac{\phi_{nmr} - H_f}{H_g P_g - H_f} \quad (29)$$

Figure 1:
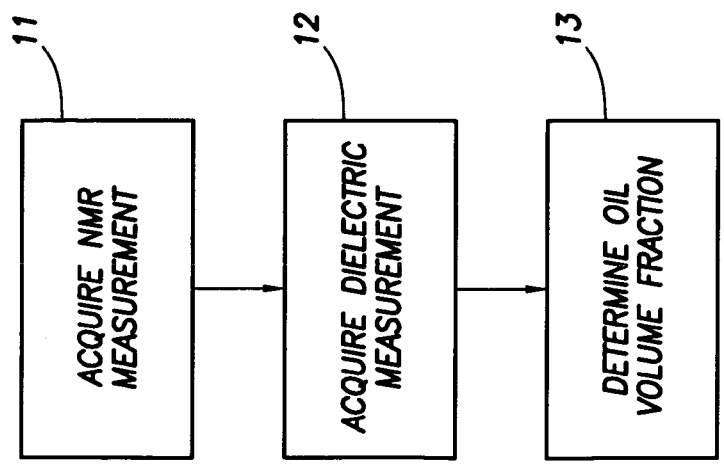
FIG. 1 is a flow chart showing one embodiment of a method according to an embodiment of the disclosed subject matter.

FIG. 1 shows one aspect of the method according to an embodiment of the disclosed subject matter. The method according to this aspect of the disclosed subject matter comprises acquiring an NMR measurement of the formation fluids 11, acquiring a dielectric measurement of the formation fluids 12, and determining an oil volume fraction from the NMR property and the dielectric property 13. Those having skill in the art will realize that the order of measuring the NMR property 11 and measuring the dielectric property 12 is not important. The disclosed subject matter is not intended to be limited by the order of the measurements. In some embodiments the NMR measurement comprises at least one spin-echo amplitude. In one embodiment, the spin-echo amplitudes are measured by selecting a polarization time sufficiently long so that oil and water in the formation fluids are substantially polarized. In some other embodiments, the dielectric measurement comprises an electromagnetic wave phase shift or attenuation.

In some embodiments of the disclosed subject matter, the formation fluids comprise fluids in the formation. In these embodiments, the total fraction of formation fluids comprises the total formation porosity $\phi$, the water volume fraction comprises the water-filled porosity $\phi_w$ of the formation, and the oil volume fraction comprises the oil-filled porosity $\phi_o$ of the formation. The oil-filled porosity can be calculated by subtracting the water-filled porosity from the total formation porosity. In one embodiment, acquiring the NMR measurement and acquiring the dielectric measurement are performed while drilling.

In some other embodiments of the disclosed subject matter, the formation fluids comprise at least one sample taken from a formation traversed by a borehole. Fluid samples can be withdrawn from the formation using any suitable device known in the art, for example, the Schlumberger MDT tool, as described in U.S. Pat. No. 4,860,581 issued to Zimmerman et al. When measurements are made on a fluid sample, the sum of the oil volume fraction and the water volume fraction is taken to be one. Because the sample has been extracted from the formation, the formation porosity can be taken to be one for purposes of sample evaluation. That is, the fluids occupy the entire volume of investigation because there is no formation in the sample.

In some embodiments, the method includes measuring an electromagnetic wave attenuation $A_c$. In one embodiment, the salinity s of the brine in the formation is determined from the electromagnetic wave attenuation and a known aqueous phase attenuation function with respect to the salinity s and the formation temperature T. The formation temperature T can be directly measured or estimated using techniques known in the art.

FIG. 2 shows another aspect of an embodiment of the disclosed subject matter. The method according to this aspect of the disclosed subject matter includes acquiring an NMR measurement 21, acquiring a dielectric measurement 22, acquiring a bulk density measurement 23, and solving a set of linear response equations representing a reservoir fluid model to determine fractional fluid volumes 24. Again, it is noted that the order of the measurements is not important and is not intended to limit the scope of the disclosed subject matter. In some embodiments, the set of linear response equations comprises Equations 13–15, described above.

The reservoir fluid model and the associated response equations are determined based on what formation fluids are expected or known to be in the formation. Information about the formation can be derived from previous measurements, other boreholes drilled in the area, and any other means known in the art to predict what fluids are present in a given formation. In some embodiments, the reservoir fluid model comprises an oil-bearing formation traversed by a borehole drilled using an oil-based mud. The model in these embodiments is selected to solve for the water volume fraction, the oil volume fraction, and the oil-based mud filtrate volume fraction.

It is noted that if the properties of the oil-based mud, e.g. the hydrogen indices and the density, do not have sufficient contrast from the properties of the oil in the formation, the volume fractions of the oil and the oil-based mud filtrate cannot be separately determined. In those cases, Equations 13–15 can be solved for i=1 to 2, where the fluid volumes to be determined are the water volume fraction and the sum of the oil and oil-based mud filtrate volume fractions. Those having skill in the art will realize that the properties of the drilling mud can be controlled so as to have different properties from the oil in the formation, thereby allowing the measurement to differentiate between the native oil and the oil-based mud filtrate.

In some embodiments of the disclosed subject matter, the formation fluids comprise fluids in a formation traversed by a borehole. In these embodiments, the water volume fraction comprises the water-filled porosity $\phi_w$ of the formation, the oil volume fraction comprises the oil-filled porosity $\phi_o$ of the formation, and the oil-based mud filtrate volume fraction comprises the oil-based mud filtrate porosity $\phi_{obmf}$ of the formation. In these embodiments, the oil-filled porosity $\phi_o$, the water-filled porosity $\phi_w$, and the oil-based mud filtrate porosity $\phi_{obmf}$ can be summed to give the total formation porosity $\phi$. In one embodiment, the method also includes measuring an electromagnetic wave attenuation $A_c$ and calculating the salinity s of the connate water in the formation based on the total formation porosity $\phi$ and a known aqueous phase attenuation function with respect to the connate water salinity s and the formation temperature T.

In some embodiments, the formation fluids comprise at least one sample withdrawn from the formation. The sum of the oil volume fraction, the water volume fraction, and the oil-based mud filtrate volume fraction are taken to be one.

Further, it is known in the art to use a sensor, for example an optical sensor, to monitor the fluids being withdrawn from the formation until the fluids are no longer changing. At that point, the extracted fluids are assumed to be comprised of native fluids. Thus, in one embodiment, the oil-based mud filtrate volume fraction is taken to be zero.

In some embodiments, the reservoir fluid model comprises a gas-bearing formation. Equations 13–15 can be solved for the gas volume fraction, the water volume fraction, and the gas-corrected total volume fraction. In one embodiment, the formation fluids comprise fluids in a formation. In this embodiment, the gas volume fraction comprises the gas-filled porosity $\phi_g$, the water volume fraction comprises water-filled porosity $\phi_w$, and the gas-corrected total volume fraction comprises the gas-corrected total formation porosity $\phi$.

In another embodiment, the formation fluids comprise at least one fluid sample withdrawn from the formation. The sum of the gas volume fraction and the water volume fraction is taken to be one.

Figure 3:
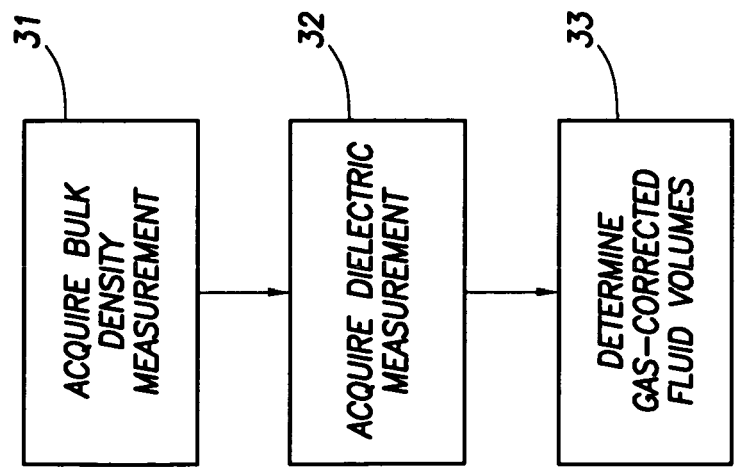
FIG. 3 is a flow chart showing another embodiment of a method according to an embodiment of the disclosed subject matter.

FIG. 3 shows another aspect of an embodiment of the disclosed subject matter. This aspect of the disclosed subject matter includes a method for evaluating formation fluids from a gas-bearing formation. The method according to this aspect includes measuring a bulk density 31, measuring a dielectric property 32, and solving the response equations for the gas corrected fluid volume 33. This aspect of the disclosed subject matter takes advantage of the opposite response of a dielectric measurement and a density measurement in the presence of gas. Again, as is known in the art, the exact order of measurement is not intended to limit the disclosed subject matter.

In some embodiments, the formation fluids comprise fluids in a formation traversed by a borehole. In these embodiments, the bulk density comprises a formation bulk density $\rho_b$, the dielectric property comprises a formation travel time $t_{pl}$, and the gas-corrected fluid volume comprises the gas-corrected total formation porosity $\phi$.

In some other embodiments, the formation fluids comprise at least one fluid sample extracted from a formation traversed by a borehole. In these embodiments, the sum of the gas volume fraction and the water volume fraction is taken to be one.

Figure 4:
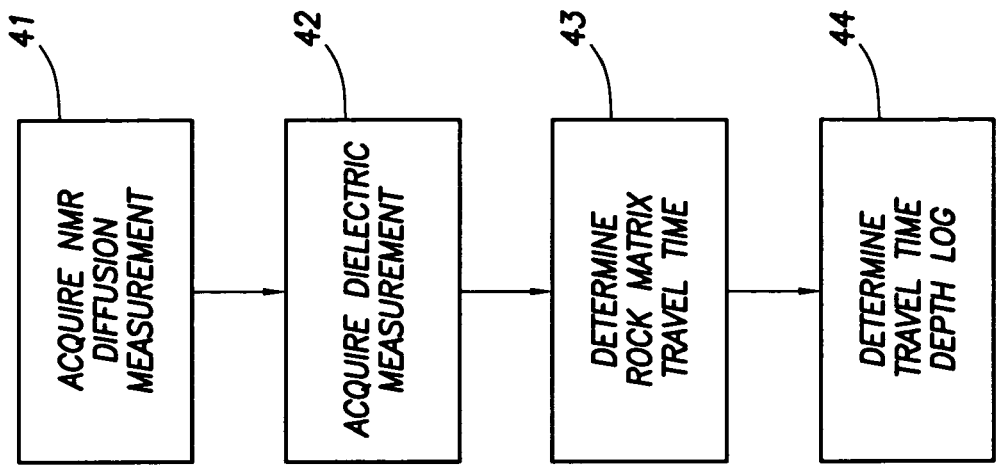
FIG. 4 is a flow chart showing another embodiment of a method according to an embodiment of the disclosed subject matter.

FIG. 4 shows another aspect according to an embodiment of the disclosed subject matter. A method according to this aspect of the disclosed subject matter includes acquiring an NMR measurement 41, acquiring a dielectric property measurement 42 related to the formation travel time $t_{pl}$, and determining a rock-matrix travel time $t_{pma}$ 43 from the NMR measurement and the dielectric property measurement. In some embodiments, the method includes determining a rock-matrix travel time log as a function of borehole depth 44.

The determination of the reservoir fluid model allows the derivation of the associated dielectric travel time equation response equation. For example, if the model comprises a formation with oil and water, the dielectric travel time response equation may have the form of Equation 3. If the model comprises a gas-bearing formation, the travel time response equation can be adjusted for the constituents of the formation, as is known in the art. Again, the dielectric mixing law is a matter of choice and is not intended to limit the disclosed subject matter.

Figures 5, 6:
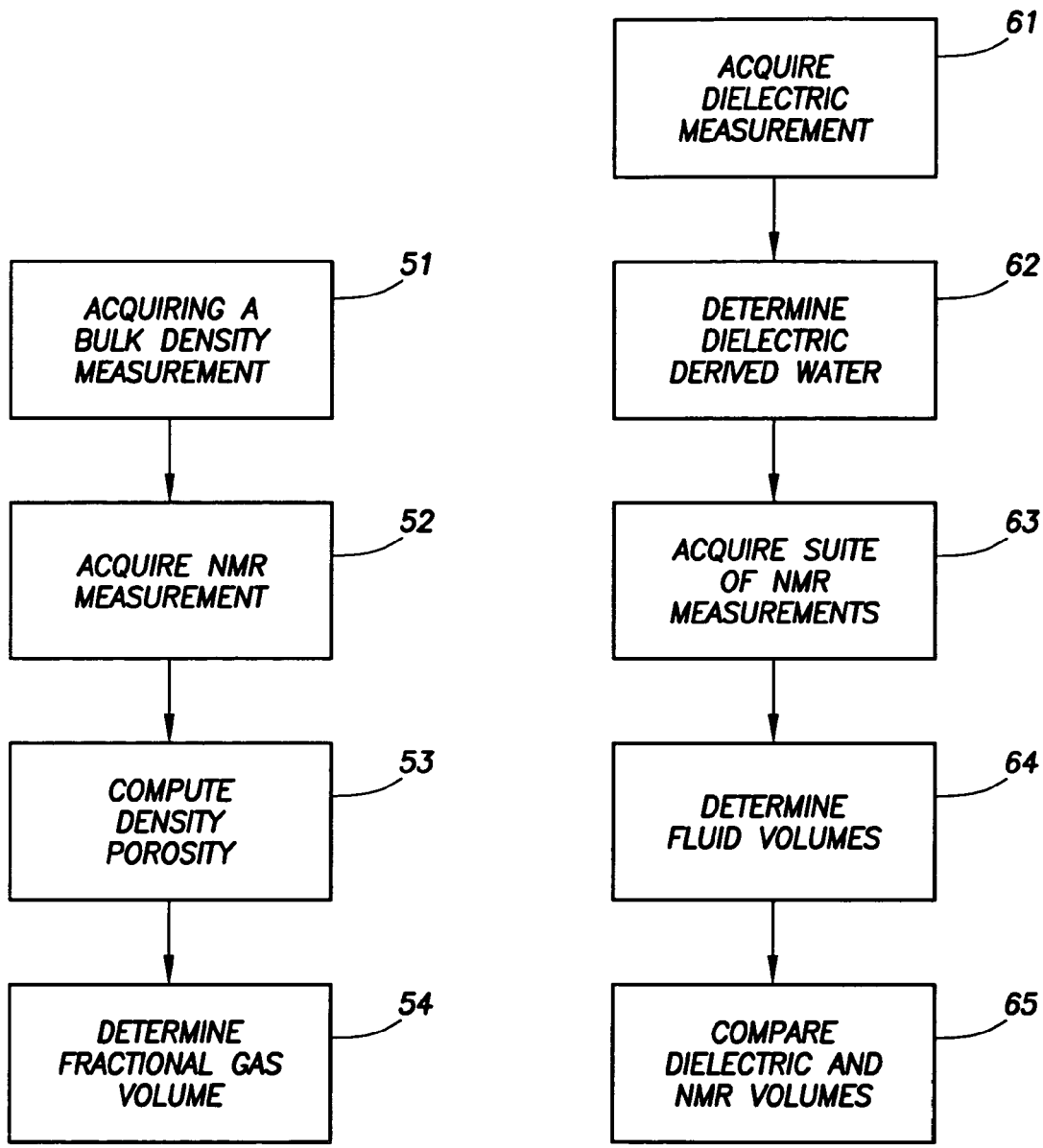
FIG. 5 is a flow chart showing another embodiment of a method according to an embodiment of the disclosed subject matter.
FIG. 6 is a flow chart showing another embodiment of a method according to an embodiment of the disclosed subject matter.

FIG. 5 shows yet another aspect of an embodiment of the disclosed subject matter for evaluating a gas-liquid sample. This aspect includes acquiring a bulk density measurement 51 and acquiring an NMR measurement 52. In one embodiment, the method according to this aspect also includes computing a density porosity from the bulk density and a fluid density 53. Equation 27 shows one example of a calculation that can be used to compute the density porosity. The method also includes determining the fractional volume of gas in the sample from the bulk density measurement and the NMR measurement 54, as for example in Equation 26. In the embodiment where the density porosity is computed, the method includes determining the fractional volume of gas in the sample from the density porosity and the NMR measurement 54.

NMR methods are capable of providing fluid properties, (e.g., volumes) for individual components in a mixture of formation fluids. For example, U.S. Pat. No. 6,229,308 B1 issued to Freedman discloses a magnetic resonance fluid characterization (MRF) method that can provide various NMR parameters for individual fluid components from a suite of NMR measurements made on a mixture of fluids. This patent is assigned to the same assignee as the present invention and is hereby incorporated by reference.

The MRF method uses differing diffusion properties to differentiate different fluid components in a mixture. The diffusion-based NMR methods, however, cannot reliably differentiate heavy oil from water in small pore spaces or water bound in clays because of poor sensitivity to the diffusion of these fluids. In some cases, NMR diffusion methods mistake water in small pore spaces or bound in clay for heavy oils. In these cases, diffusion-based NMR methods will predict a non-negligible oil volume in formations where there is no oil. A dielectric measurement, however, is not affected by the viscosity of heavy oil and can provide more accurate determination of the water volume. The dielectric derived water volume can be compared with the individual fluid volumes derived from diffusion-based NMR methods to provide a more accurate estimate of the water and heavy oil volumes. For example, an apparent heavy oil volume and water volume may first be derived from the suite of NMR measurements. The water volume derived from the dielectric measurement is then compared with the water volume and the apparent heavy oil volume derived from the suite of NMR measurements. The comparison will yield the true heavy oil volume, i.e., the contribution of water in the apparent heavy oil volume can be removed using this comparison.

FIG. 6 shows another aspect of a method according to an embodiment of the disclosed subject matter. The method includes acquiring dielectric measurements 61, and determining a dielectric-derived water volume from the dielectric measurements 62. The method also includes acquiring a suite of NMR measurements 63 and deriving a water volume and an apparent heavy oil volume from the suite of NMR measurements 64. The method next includes comparing the dielectric derived water volume with NMR derived water volume and the apparent heavy oil volume to produce a true heavy oil volume 65.

The following are some of the possible advantages of an embodiment of the disclosed subject matter. The method according to an embodiment of the disclosed subject matter provides fluid volumes that are independent of the magnetic field gradient of the NMR logging instrument because it does not rely on contrasts in molecular diffusion coefficients to differentiate formation fluids. For example, NMR methods are uncertain for some cases in formations with high concentrations of iron-rich minerals, such as chlorite clay, that have strong internal magnetic field gradients. In formations that have a high internal magnetic field gradient, such as North Burbank sandstone, the accuracy of diffusion-based methods is also reduced. Also, in some cases NMR methods have difficulty in differentiating very viscous oils, over about 100 centipoise, from clay-bound water and water in small pore spaces. Using the dielectric travel time and attenuation measurements in conjunction with NMR measurements provides an improvement because the dielectric measurements are not effected by oil viscosity. Dielectric logs can be used in reservoirs containing heavy oils with a viscosities that exceed thousands of centipoise. In these environments, diffusion-based NMR methods provide reduced accuracy oil volumes. The method according to an embodiment of the disclosed subject matter is also more reliable than stand-alone dielectric log interpretation because an embodiment of the disclosed subject matter is less dependent on rock matrix travel times that are functions of unknown lithology and mineralogy. The combination of dielectric, NMR, and density logs according to an embodiment of the disclosed subject matter can overcome these limitations of the prior art.

Also, the combination of dielectric and density measurements in a gas-bearing formation provides more accurate data because they have an opposite response to the presence of gas, allowing for the presence of gas to be detected.

While the disclosed subject matter has been described with respect to a limited number of embodiments, those skilled in the art, having benefit of this disclosure, will appreciate that other embodiments can be devised which do not depart from the scope of the disclosed subject matter as disclosed herein. Accordingly, the scope of the disclosed subject matter should be limited only by the attached claims.

What is claimed is:

1. A method for determining a gas fractional volume in a gas-liquid sample, comprising:
    acquiring a nuclear magnetic resonance measurement from the gas-liquid sample;
    acquiring a bulk density measurement from the gas-liquid sample separate from the nuclear magnetic resonance measurement; and
    determining the gas fractional volume of the gas-liquid sample directly from a combination of the bulk density measurement and the nuclear magnetic resonance measurement.

2. The method of claim 1, further comprising computing a density porosity from the bulk density measurement and a fluid density, and wherein the determining the gas fractional volume is performed using the density porosity and the nuclear magnetic resonance measurement.

* * * * *